United States Patent [19]
Wellman

[11] Patent Number: 6,042,189
[45] Date of Patent: Mar. 28, 2000

[54] RESTRAINT FREE WHEELCHAIR SYSTEM

[76] Inventor: Mary C. Wellman, 1916 Whitehouse Dr., Montrose, Colo. 81402

[21] Appl. No.: 09/097,986

[22] Filed: Jun. 16, 1998

[51] Int. Cl.[7] .................................................. A47C 31/00
[52] U.S. Cl. .................... 297/465; 297/466; 297/DIG. 4; 297/DIG. 6; 280/290
[58] Field of Search .............................. 297/DIG. 6, 465, 297/DIG. 4, 464, 466; 2/912, 917, 919, 1, 69, 456, 250.1; 280/290

[56] References Cited

U.S. PATENT DOCUMENTS

| | | |
|---|---|---|
| 3,136,311 | 6/1964 | Lewis . |
| 4,639,946 | 2/1987 | Koenig . |
| 4,807,937 | 2/1989 | Harrigan . |
| 4,898,185 | 2/1990 | Fuller . |
| 5,023,125 | 6/1991 | Gray . |
| 5,149,173 | 9/1992 | Jay et al. . |
| 5,426,801 | 6/1995 | Klearman et al. . |
| 5,620,227 | 4/1997 | Brune . |
| 5,816,662 | 10/1998 | Rumburg . |
| 5,829,840 | 11/1998 | Goeckel . |

*Primary Examiner*—Milton Nelson, Jr.

[57] ABSTRACT

A restraint free wheelchair system is provided including a wheelchair having a pile fastener attached thereto. A piece of clothing is included with a pile fastener attached thereto for releasably securing to the pile fastener of the wheelchair.

10 Claims, 4 Drawing Sheets

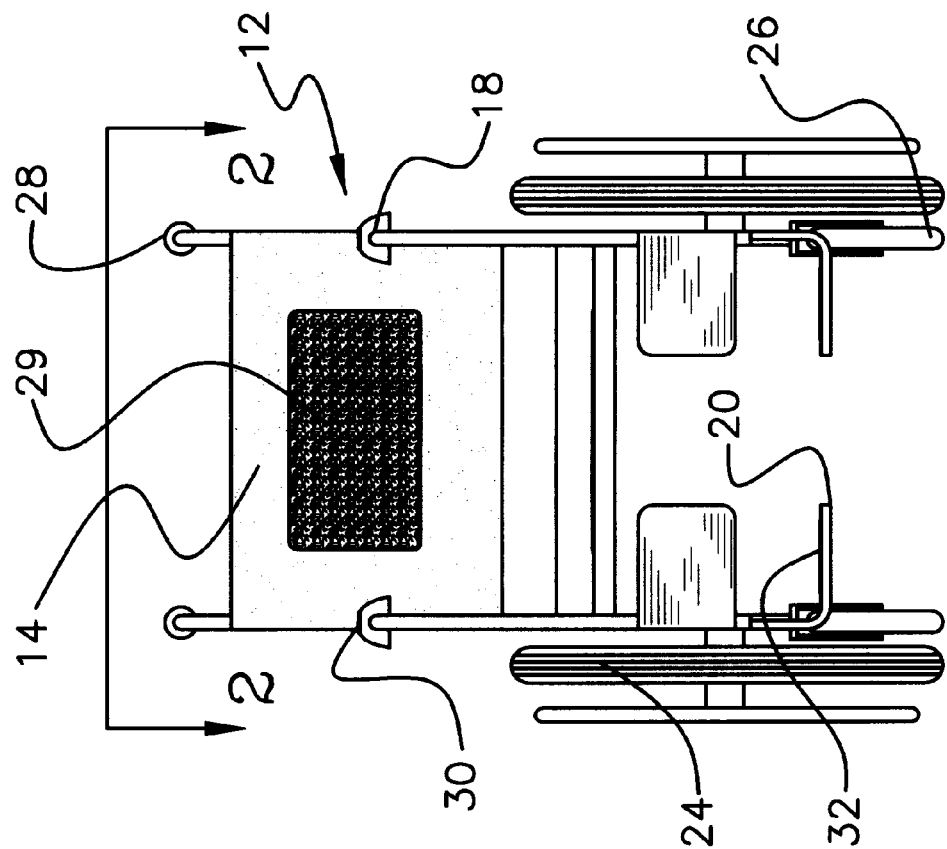
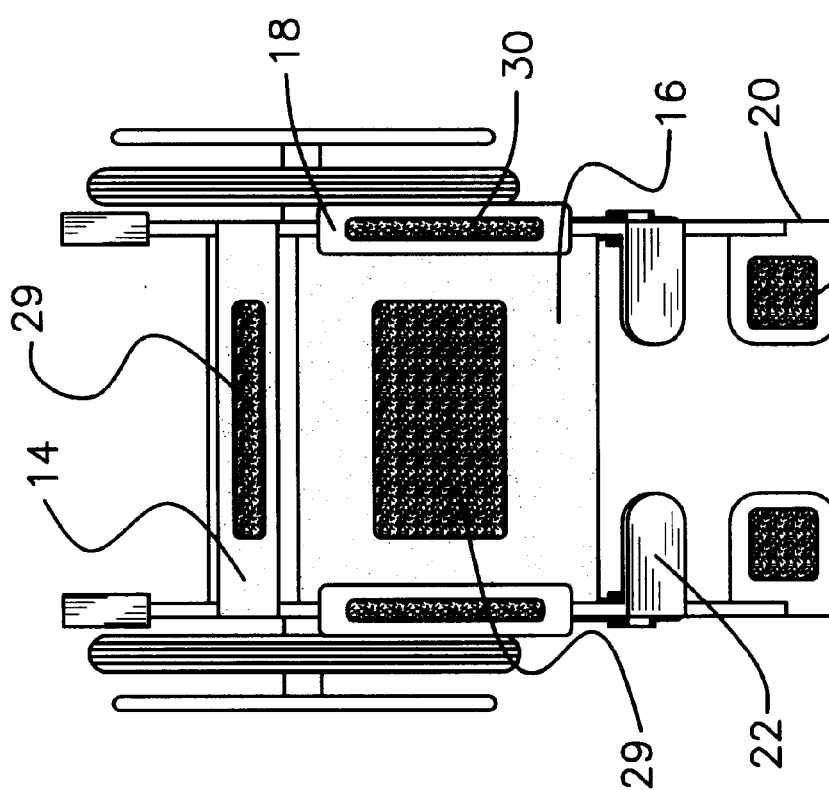

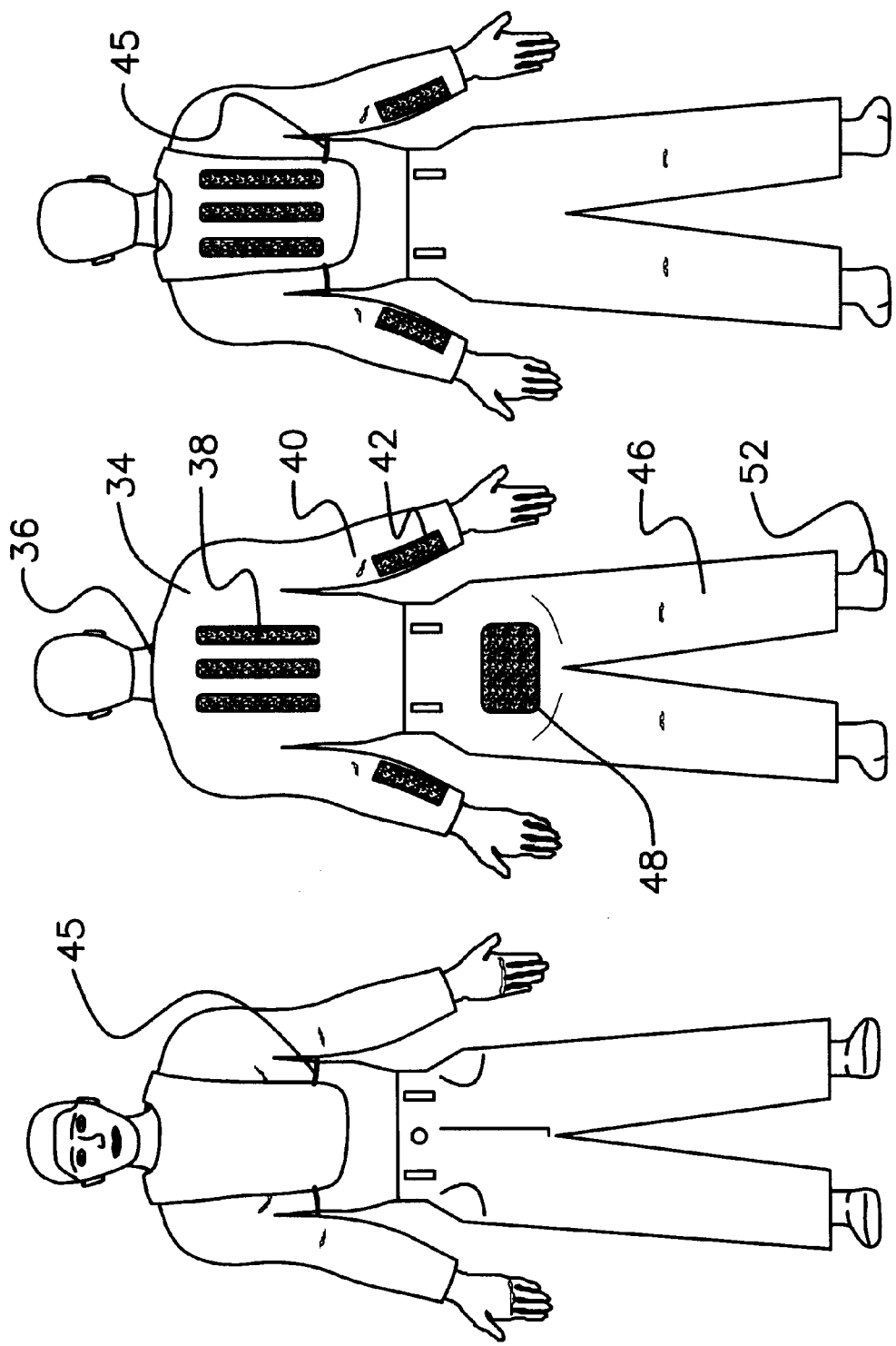

RESTRAINT FREE WHEELCHAIR SYSTEM

BACKGROUND OF THE INVENTION

1. Field of the Invention

The present invention relates to restraint free devices particularly pertains to a new restraint free wheelchair system for preventing a person within a wheelchair from incurring injury.

2. Description of the Prior Art

The use of restraint free devices is known in the prior art. More specifically, restraint free devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art restraint free devices include U.S. Pat. No. 4,807,937; U.S. Pat. No. 4,177,807; U.S. Pat. Des. 341,661; U.S. Pat. No. 4,787,101; U.S. Pat. No. 5,248,182; and U.S. Pat. No. 4,685,454.

In these respects, the restraint free wheelchair system according to the present invention substantially departs from the conventional concepts and designs of the prior art, and in so doing provides an apparatus primarily developed for the purpose of preventing a person within a wheelchair from incurring injury.

SUMMARY OF THE INVENTION

In view of the foregoing disadvantages inherent in the known types of restraint free devices now present in the prior art, the present invention provides a new restraint free wheelchair system construction wherein the same can be utilized for preventing a person within a wheelchair from incurring injury.

The general purpose of the present invention, which will be described subsequently in greater detail, is to provide a new restraint free wheelchair system apparatus and method which has many of the advantages of the restraint free devices mentioned heretofore and many novel features that result in a new restraint free wheelchair system which is not anticipated, rendered obvious, suggested, or even implied by any of the prior art restraint free devices, either alone or in any combination thereof.

To attain this, the present invention generally comprises a seat portion with a back rest having a front face and a rear face. Associated therewith is a bottom rest having a top face and a bottom face. The seat portion further includes a pair of arm rests mounted on opposite sides of the seat portion each with a top face. A pair of foot portions each have an L-shaped vertical cross-section with a top face and a bottom face. A pair of large rear wheels are rotatably mounted about a fixed axis at a rear extent of the seat portion. A pair of small front wheels are rotatably mounted about a variable horizontal axis at a front extent of the seat portion. Lastly, a pair of handles are coupled to a top extent of the seat portion and extend rearwardly therefrom. Also included is a first pair of rectangular pile fasteners with a long first length and a short first width. Each of such pile fasteners are attached to the front face of the back rest of the wheelchair and the top face of the bottom rest of the wheelchair, respectively. See FIGS. 2 & 3. A second pair of rectangular pile fasteners are provided with the first length and a second width which is less than the first width. As best shown in FIG. 2, the pile fasteners of the second pair are attached to the top faces of the arm rests. Shown in FIG. 2 is a third pair of square pile fasteners each with an equal length and width. The square pile fasteners are attached to the top faces of the foot rests. FIG. 5 shows an upper body garment having a rectangular rear portion integrally coupled to a rectangular front portion with an aperture formed therebetween. The apertures serves for allowing a head of a user to pass therethrough. An outer surface of the rear portion has a plurality of spaced thin vertical strips of pile fasteners attached thereto between the aperture and a bottom edge thereof. Each thin vertical strip of pile fastener has a length greater than the first width. The upper body garment further has elongated sleeves each with a pile fastener attached to a bottom side thereof adjacent to ends thereof. During use, the thin vertical strips are removably secured to the pile fastener attached to the back rest of the wheelchair. Further, the pile fasteners attached to the sleeves are removably secured to the pile fasteners attached to the arm rests of the wheelchair. Also included is a pair of pants with a seat having a rectangular pile fastener attached to an outer surface thereof. The pile fastener of the pair of pants has the first length and the first width. In use, the pile fastener of the pair of pants is removably coupled secured to the pile fastener attached to the bottom rest of the wheelchair. Finally, a pair of shoes are provided each having a sole with a bottom surface having a square pile fastener attached thereto. Such pile fasteners are removably coupled secured to the pile fasteners attached to the foot rests of the wheelchair.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new restraint free wheelchair system apparatus and method which has many of the advantages of the restraint free devices mentioned heretofore and many novel features that result in a new restraint free wheelchair system which is not anticipated, rendered obvious, suggested, or even implied by any of the prior art restraint free devices, either alone or in any combination thereof.

It is another object of the present invention to provide a new restraint free wheelchair system which may be easily and efficiently manufactured and marketed.

It is a further object of the present invention to provide a new restraint free wheelchair system which is of a durable and reliable construction.

An even further object of the present invention is to provide a new restraint free wheelchair system which is susceptible of a low cost of manufacture with regard to both materials and labor, and which accordingly is then susceptible of low prices of sale to the consuming public, thereby making such restraint free wheelchair system economically available to the buying public.

Still yet another object of the present invention is to provide a new restraint free wheelchair system which provides in the apparatuses and methods of the prior art some of the advantages thereof, while simultaneously overcoming some of the disadvantages normally associated therewith.

Still another object of the present invention is to provide a new restraint free wheelchair system for preventing a person within a wheelchair from incurring injury.

Even still another object of the present invention is to provide a new restraint free wheelchair system that includes a wheelchair having a pile fastener attached thereto. A piece of clothing is included with a pile fastener attached thereto for releasably securing to the pile fastener of the wheelchair.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 2 is a top view of the present invention.

FIG. 3 is a front view of the present invention.

FIG. 4 is a front view of a first embodiment of the upper garment of the present invention.

FIG. 5 is a rear view of the second embodiment of the upper garment of the present invention.

FIG. 6 is a rear view of the first embodiment of the upper garment of the present invention.

DESCRIPTION OF THE PREFERRED EMBODIMENT

Figure 1:
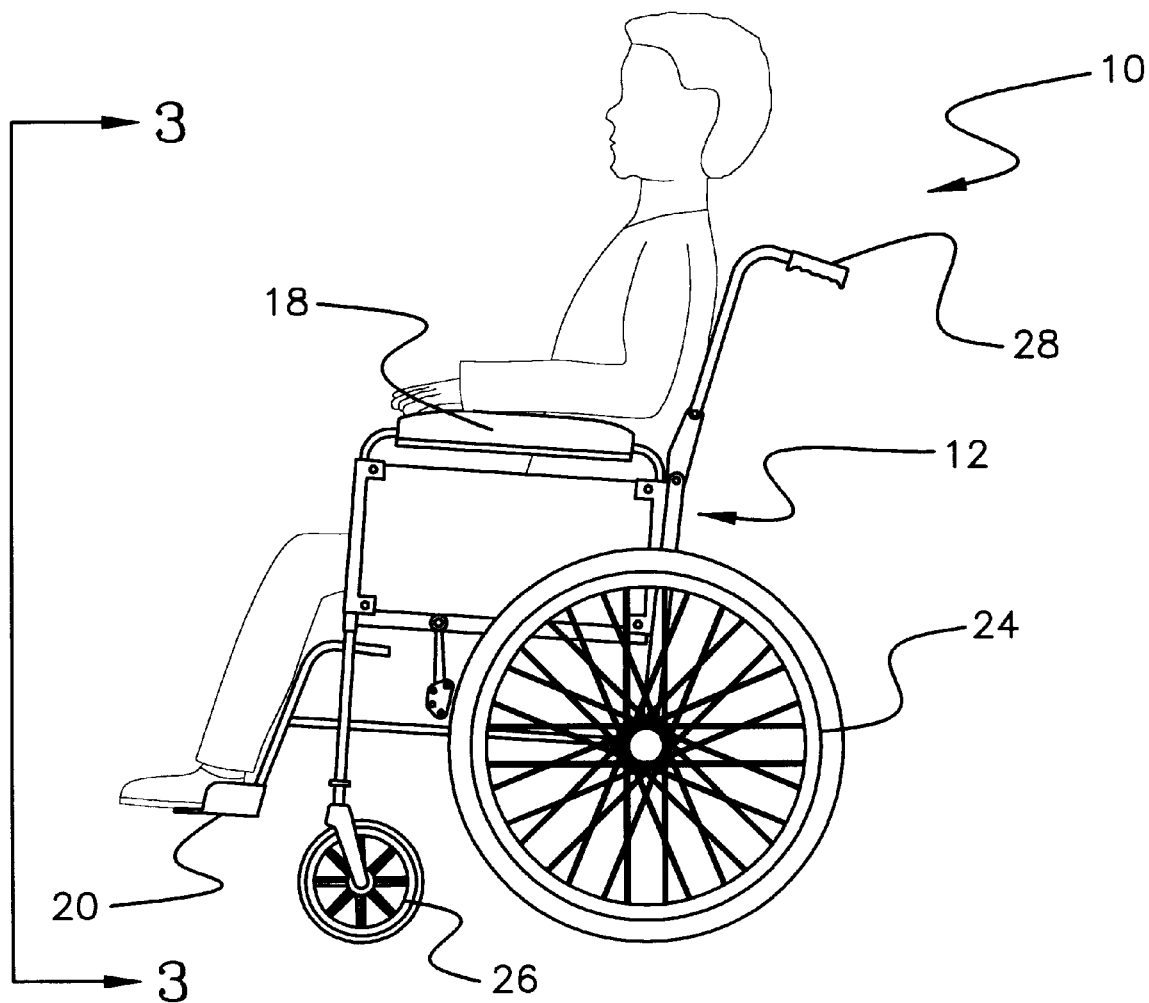
FIG. 1 is a side view of a new restraint free wheelchair system according to the present invention.
Figure 9:
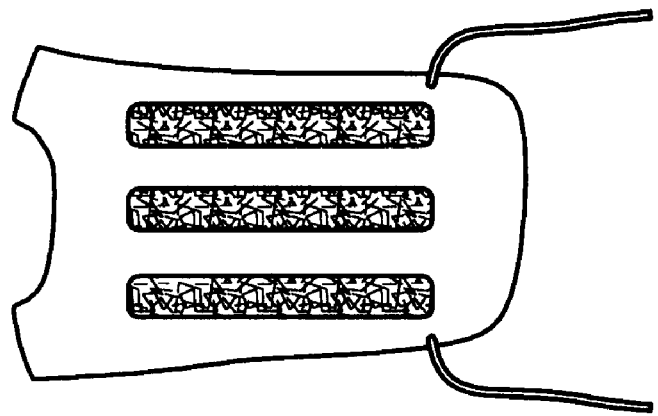
FIG. 9 is a rear view of the upper body garment of the FIGS. 4 & 6.
Figure 8:
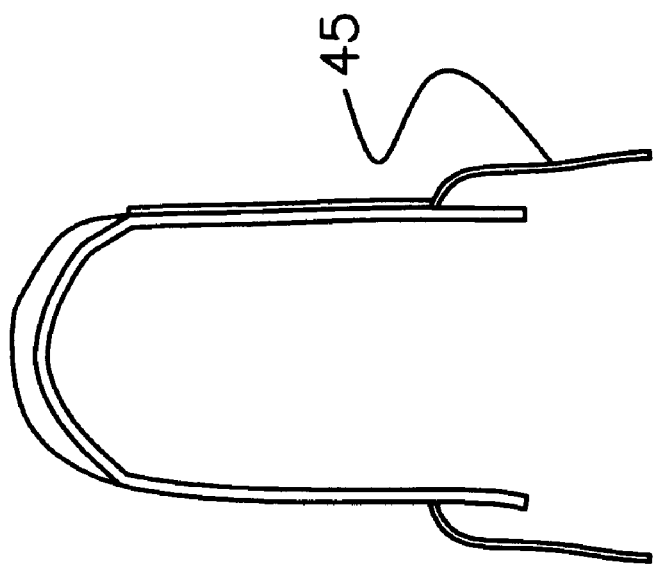
FIG. 8 is a side view of the upper body garment of the FIGS. 4 & 6.
Figure 7:
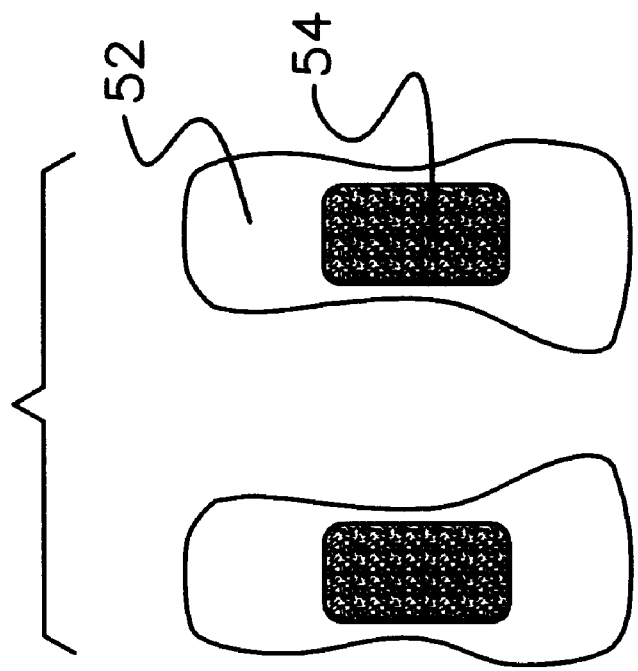
FIG. 7 is a bottom view of the shoes of the present invention.

With reference now to the drawings, and in particular to FIGS. 1 through 9 thereof, a new restraint free wheelchair system embodying the principles and concepts of the present invention and generally designated by the reference numeral 10 will be described.

The present invention, as designated as numeral 10, includes a seat portion 12 with a back rest 14 having a front face and a rear face. Associated therewith is a bottom rest 16 having a top face and a bottom face. The seat portion further includes a pair of arm rests 18 mounted on opposite sides of the seat portion each with a top face. A pair of foot portions 20 each have an L-shaped vertical cross-section with a top face and a bottom face. A rear leg rest 22 is mounted above each of the foot portions for supporting a calf of a leg.

A pair of large rear wheels 24 are rotatably mounted about a fixed axis at a rear extent of the seat portion. A pair of small front wheels 26 are rotatably mounted about a variable horizontal axis at a front extent of the seat portion. Lastly, a pair of handles 28 are coupled to a top extent of the seat portion and extend rearwardly therefrom.

Also included is a first pair of rectangular pile fasteners 29 with a long first length and a short first width. Each of such pile fasteners are attached to the front face of the back rest of the wheelchair and the top face of the bottom rest of the wheelchair, respectively. See FIGS. 2 & 3. An area defined by the first pair of rectangular pile fasteners is about ½ that of the respective rest of the seat portion.

A second pair of rectangular pile fasteners 30 are provided with the first length and a second width which is less than ¼ that of the first width. As best shown in FIG. 2, the pile fasteners of the second pair are attached to the top faces of the arm rests and cover nearly an entirety of such top faces.

Shown in FIG. 2 is a third pair of square pile fasteners 32 each with an equal length and width. The square pile fasteners are attached to the top faces of the foot rests at a central extent thereof.

FIG. 5 shows an upper body garment 34 having a rectangular rear portion integrally coupled to a rectangular front portion with an aperture 36 formed therebetween. The apertures serves for allowing a head of a user to pass therethrough. An outer surface of the rear portion has a plurality of spaced thin vertical strips of pile fasteners 38 attached thereto between the aperture and a bottom edge thereof. Each thin vertical strip of pile fastener has a length greater than the first width.

The upper body garment further has elongated sleeves 40 each with a pile fastener 42 attached to a bottom side thereof adjacent to ends thereof. Such pile fasteners of the sleeves each have a width which is twice that of the second pair of pile fasteners associated with the arm rests. During use, the thin vertical strips of pile fasteners are removably secured to the pile fastener of the first pair attached to the back rest of the wheelchair. Further, the pile fasteners attached to the sleeves are removably secured to the second pair of pile fasteners attached to the arm rests of the wheelchair.

In another embodiment, the rear portion and the front portion of the upper body garment are separate and have a pair strings 45 coupled to side edges thereof adjacent the respective bottom edges. The rear portion and front portion of the upper body garment may thus be secured about a torso of a user. Note FIGS. 4 & 6.

Also included is a pair of pants 46 with a seat having a rectangular pile fastener 48 attached to an outer surface thereof. The pile fastener of the pair of pants has the first length and the first width. In use, the pile fastener of the pair of pants is removably coupled secured to the pile fastener of the first pair attached to the bottom rest of the wheelchair. As an option, the seat of the pants may have a cushioning pad mounted thereon.

Finally, a pair of shoes 52 are provided each having a sole with a bottom surface having a square pile fastener 54 attached thereto. Ideally, the pile fasteners of the shoes are each of a similar size and shape as those of the foot rests of the wheelchair. Such pile fasteners are removably coupled secured to the third pair of pile fasteners attached to the foot rests of the wheelchair. Similar to the coupling between the previous pile fasteners, the present coupling precludes sliding within the chair, dangling of appendages, and further prevents the user from being inadvertently removed from the wheelchair.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A restraint free wheelchair system comprising, in combination:
    a wheelchair including a seat portion with a back rest having a front face and a rear face and a bottom rest having a top face and a bottom face, a pair of arm rests mounted on opposite sides of the seat portion, each arm rest having a top face, a pair of foot portions each having an L-shaped vertical cross-section with a top face and a bottom face, a pair of large rear wheels rotatably mounted about a fixed axis at a rear extent of the seat portion, a pair of small front wheels rotatably mounted about a variable horizontal axis at a front extent of the seat portion, and a pair of handles coupled to a top extent of the seat portion and extending rearwardly therefrom;
    a first pair of rectangular pile fasteners with a long first length and a short first width, one of the pile fasteners of the first pair of pile fasteners being attached to the front face of the back rest of the wheelchair and the other pile fastener of the first pair of pile fasteners being attached to the top face of the bottom rest of the wheelchair;
    a second pair of rectangular pile fasteners with the first length and a second width which is less than the first width, the pile fasteners of the second pair being attached to the top faces of the arm rests;
    a third pair of square pile fasteners with an equal length and width attached to the top faces of the foot portions;
    an upper body garment having a rectangular rear portion integrally coupled to a rectangular front portion with an aperture formed therebetween for allowing a head of a user to pass therethrough, an outer surface of the rear portion having a plurality of spaced thin vertical strips of pile fasteners attached thereto between the aperture and a bottom edge thereof, each thin vertical strip of pile fastener having a length greater than the first width, the upper body garment further having elongated sleeves each with a pile fastener attached to a bottom side thereof adjacent to ends thereof, whereby the thin vertical strips are removably secured to the pile fastener attached to the back rest of the wheelchair and the pile fasteners attached to the sleeves are removably secured to the pile fasteners attached to the arm rests of the wheelchair;
    a pair of pants with a seat having a rectangular pile fastener attached to an outer surface thereof, the pile fastener of the pair of pants having the first length and the first width, whereby the pile fastener of the pair of pants is removably secured to the pile fastener attached to the bottom rest of the wheelchair; and
    a pair of shoes each having a sole with a bottom surface having a square pile fastener attached thereto, whereby the pile fasteners of the pair of shoes are removably secured to the pile fasteners attached to the foot portions of the wheelchair.

2. A restraint free wheelchair system comprising:
    a wheelchair having a pile fastener attached thereto;
    a piece of clothing with a pile fastener attached thereto for releasably securing to the pile fastener of the wheelchair; and
    wherein the pile fastener of the wheelchair is attached to a bottom rest of a seat portion thereof and the pile fastener of the piece of clothing is attached to a rear extent thereof, wherein the piece of clothing is a pair of pants.

3. A restraint free wheelchair system as set forth in claim 2 additionally comprising a pile fastener attached to a back rest of a seat portion of the wheelchair and a pile fastener is attached to a rear extent of a second piece of clothing, wherein the second piece of clothing is an upper body garment.

4. A restraint free wheelchair system as set forth in claim 3 wherein the upper body garment has a rectangular rear portion integrally coupled to a rectangular front portion with an aperture formed therebetween for allowing a head of a user to pass therethrough, the rear portion and the front portion each having a pair strings coupled to side edges thereof adjacent to the bottom edge of the portion.

5. A restraint free wheelchair system as set forth in claim 2 additionally comprising a pile fastener attached to arm rests of the wheelchair and a pile fastener is attached to sleeves of a second piece of clothing, wherein the second piece of clothing is an upper body garment.

6. A restraint free wheelchair system as set forth in claim 2 additionally comprising a pile fastener attached to foot rests of the wheelchair and a pile fastener is attached to a bottom of a second piece of clothing, wherein the second piece of clothing is a pair of shoes.

7. A restraint free wheelchair system comprising:
    a wheelchair having a pile fastener attached thereto;
    a piece of clothing with a pile fastener attached thereto for releasably securing to the pile fastener of the wheelchair; and
    wherein the pile fastener of the wheelchair is attached to arm rests thereof and the pile fastener of the piece of clothing is attached to sleeves thereof, wherein the piece of clothing is an upper body garment.

8. A restraint free wheelchair system as set forth in claim 7 wherein the upper body garment has a rectangular rear portion integrally coupled to a rectangular front portion with an aperture formed therebetween for allowing a head of a user to pass therethrough, the rear portion and the front portion each having a pair of strings coupled to side edges thereof adjacent to the bottom edge of the portion.

9. A restraint free wheelchair system as set forth in claim 7 additionally comprising a pile fastener attached to a back rest of a seat portion of the wheelchair and a pile fastener is attached to a rear extent of the upper body garment.

10. A restraint free wheelchair system as set forth in claim 7 additionally comprising a pile fastener attached to foot rests of the wheelchair and a pile fastener is attached to a bottom of a second piece of clothing, wherein the second piece of clothing is a pair of shoes.

* * * * *